(12) United States Patent
Chung et al.

(10) Patent No.: US 7,368,917 B2
(45) Date of Patent: May 6, 2008

(54) ELECTRONIC CIRCUIT FOR ION SENSOR WITH BODY EFFECT REDUCTION

(75) Inventors: Wen-Yaw Chung, Taoyuan Hsien (TW); Chung-Huang Yang, Jinning Township, Kinmen County (TW); Dorota Genowefa Pijanowska, Nieporet (PL); Piotr Grabiec, Osowiec (PL); Bohdan Jaroszewicz, Warsaw (PL); Wladyslaw Torbicz, Warsaw (PL)

(73) Assignee: Chung Yuan Christian University, Chung Li (TW)

( * ) Notice: Subject to any disclaimer, the term of this patent is extended or adjusted under 35 U.S.C. 154(b) by 170 days.

(21) Appl. No.: 11/450,456

(22) Filed: Jun. 12, 2006

(65) Prior Publication Data

US 2007/0089988 A1    Apr. 26, 2007

(30) Foreign Application Priority Data

Oct. 21, 2005    (TW) .............................. 94136992 A (51) Int. Cl.
    *G01N 27/62*    (2006.01)
(52) U.S. Cl. .................. 324/459; 324/450; 702/25
(58) Field of Classification Search ................ 324/459, 324/450; 702/24, 25
    See application file for complete search history.

(56) References Cited

U.S. PATENT DOCUMENTS 4,641,249 A * 2/1987 Gion et al. ................... 702/25
4,701,253 A   10/1987 Ligtenberg et al.
6,906,524 B2 * 6/2005 Chung et al. ............... 324/464

OTHER PUBLICATIONS

S. Casans et al.,ISFET drawbacks minimization using a novel electronic compensation, 2004, Sens. Actuators, B, Chem 99 p. 42-49, no month's available.
A. Morgenshtein et al, CMOS readout circuitry for ISFET microsystems, 2004, Sens. Actuators, B, Chem 97 p. 122-131, no month's available.
W. Y. Chung et al, ISFET interface circuit embedded with noise rejection capability, 2004, Electron. Lett., 40 (18) p. 1115-1116, Sep. 2004.
A. Morgenshtein etal, Wheatstone-bridge readout interface for ISFET/REFET applications, 2004 Sens. Actuators, B, Chem 98 p. 18-27, no month's available.

(Continued)

Primary Examiner—Vincent Q. Nguyen
(74) Attorney, Agent, or Firm—Rabin & Berdo, P.C.

(57) ABSTRACT

An electronic circuit for ion sensor with the body effect reduction includes a bridge-type floating source circuit provided with an input terminal, an output terminal reflecting the change in the potential dependent on ion concentration, and an ion-sensitive field effect transistor (ISFET) wherein one terminal of the ISFET is coupled with the output terminal; a current mirror for providing a current to the bridge-type circuit; a third transistor for receiving the operating current provided by the current mirror, identical to the current provided to the ISFET; a differential amplifying circuit, wherein one input terminal of the amplifying circuit is input with a reference voltage, and the other input terminal is coupled with the output of the bridge-type readout circuit; and a third amplifier to generate a differential output voltage compensated for the body effect, temperature and time drift effects.

9 Claims, 5 Drawing Sheets

OTHER PUBLICATIONS

S. Casans et al, Novel voltage-controlled conditioning circuit applied to the ISFETs temporary drift and thermal dependency, 2003, Sens. Actuators, B, Chem 91 p. 11-16, no month's available.

S. Casans et al, Novel constant current driver for ISFET/MEMFETs characteristization, 2001, Sens. Actuators, B, Chem 76 p. 629-633, no month's available.

Y. L. Chin et al, A novel pH sensitive ISFET with on chip temperature sensing using CMOS standard process, 2001, Sens. Actuators, B, Chem 76 p. 582-593, no month's available.

B. Palan et al, New ISFET sensor interface circuit for biomedical applications, 1999, Sens. Actuators, B, Chem 57 p. 63-68, Jan. 1999.

L. Ravczzi, P. Conci, ISFET sensor coupled with CMOS read-out circuit microsystem, Electron. Lett., 34 (1998) 2234-2235, no month's available.

P. Berveld, Future applications of ISFETs, 1991, Sens. Actuators, B, Chem 4 p. 125-133, no month.

G.-H. Wang et al, ISFET temperature characteristics, 1987, Sens. Actuators, B, Chem 11 p. 221-237, no month.

T. Matsuo et al, Methods of ISFET fabrication, 1981, Sens. Actuators, B, Chem 1 p. 77-96, no month.

P. Bergveld, Development of an ion sensitive solid-state device for neurophysiological measurements, 1970, IEEE Trans. Biomed. Eng., January p. 70-71.

* cited by examiner

ELECTRONIC CIRCUIT FOR ION SENSOR WITH BODY EFFECT REDUCTION

CROSS-REFERENCE TO RELATED APPLICATIONS

This Non-provisional application claims priority under 35 U.S.C. § 119(a) on Patent Application No(s). 094136992 filed in Taiwan on Oct. 21, 2005, the entire contents of which are hereby incorporated by reference.

BACKGROUND OF THE INVENTION

1. Field of Invention

The present invention relates to an electronic circuit for an ion sensor, and more particularly to an electronic circuit for hydrogen ion sensitive transistors, configured as a bridge-type floating source with body effect reduction.

2. Related Art

The development of micro-electronic technology has enabled a very small semiconductor to respond to chemical concentrations. Ion-sensitive field effect transistor (ISFET), a kind of micro-sensing device invented by Bergveld in 1970 and developed quickly thereafter, is a solid state element consisting of a chemical sensing film and a field effect transistor. The ISFET, capable of selective measurements of concentration (activity) of certain ions in the electrolyte, is an impedance converting element, which combines the characteristics of the low output impedance of the metal oxide semiconductor field effect transistor (MOSFET) and the operation principle of the ion selective electrode (ISE). The ISFET has the advantages of short response time, batch processing ability, small sample volume, potential of single chip circuit integration, and compatibility to CMOS technology. Therefore, it is the best choice for the chemical sensor array in a large scale integrated circuit.

Comparing with the MOSFET element, in the ISFET structure, the metal or the poly silicon gate is replaced by an electrolyte and a reference electrode. Variations in the concentration of certain ions in the electrolyte result in the changes of the threshold voltage (dVTH*) of the ISFET. The changes reflecting the ion concentration in the electrolyte are recorded by a suitable electronic read-out circuit.

The manufacturing method, analysis of characteristics, and measurements of the ISFET have been widely discussed and studied. The research shows that the ISFET has some undesirable characteristics, including temperature dependence, time drift, and hysteresis, which limit the precision of measurements carried out by means of ISFETs. Furthermore, the slope of the characteristic (sensitivity) is also an important parameter describing the performance of ISFET.

The threshold voltage of ISFET will change due to the change in concentration of hydrogen ions (expressed by the pH change of the electrolyte), so that the voltage response is often used as an output signal of the ISFET. To capture the electrical signal generated by a sensor, the sensor (ISFET) must be accompanied with an analog read-out interface. The most precise measuring method by means of ISFETs is obtained under constant voltage/constant current conditions. Recently, along with the development of semiconductor technology, integration of an ISFET and a read-out interface into a chip has become an important research subject. Due to low migration and high carrier mobility, the N-channel ISFET is more often used than the P-channel ISFET. At present, in the CMOS technology, an NMOS is usually manufactured in the p-type body, and in order to make the circuit operate in a normal mode, the p-type body should usually be connected to the most negative voltage of the system. Therefore, if the ISFET and the read-out interface are integrated into the same chip, the above-mentioned read-out circuit will face the problem that the substrate potential seriously influences the real characteristics of the elements. Morgenshtein et al. proposed a new technology in 2004, which eliminates the body effect of ISFET in the read-out circuit of the integrated micro-system; however, some part of the circuit has not yet been applied to the constant voltage and constant current configuration.

Furthermore, many articles regarding compensating circuits have been published with respect to the ISFET temperature effect and time drift. Wang et al. proposed the method of zero temperature coefficient regulation and temperature coefficient compensation for reducing the temperature coefficient of the pH-ISFET. However, zero temperature coefficient regulation is more suitable for the time-controlled measurements for solutions of a specified pH range. For different ISFETs, the drain current uninfluenced by the temperature should first be determined. To compensate for the temperature and time drifts, Palan et al. applied the difference of sensitivity of ISFETs with two different sensing films (Si3N4 and Al2O3). The ISFETs were operated in a differential mode. However, there was not enough data to prove the compensating effect for this approach. Casans et al. proposed the regulating and compensating circuit controlled by voltage to eliminate the effects of time and temperature drifts. However, in this case many additional bias voltages must be provided, which increase the complexity of the system.

Some American patents have proposed methods for time and temperature drift compensation, but all those methods required additional circuits and redundant data calculation. Considering U.S. Pat. No. 4,641,249, the temperature drift compensation method required extra temperature sensors, and signal processing circuits, which adopted zero temperature regulation to calculate temperature compensation parameters. These resulted in large hardware circuits including processors, analog digital converters, digital-analog converters, random access memories, as well as read only memories, and complex calculations to be done on a computer. The time drift compensation method disclosed in the U.S. Pat. No. 4,701,253, includes ISFETs, amplifiers, and control compensating circuits, which adopts the index equation $\Delta V_p = A \ln(t/t_0 + 1)$ to correct the time drift. Likewise, the circuit disclosed in the U.S. Pat. No. 4,701,253 also requires redundant calculation and data storage.

Figure 1:
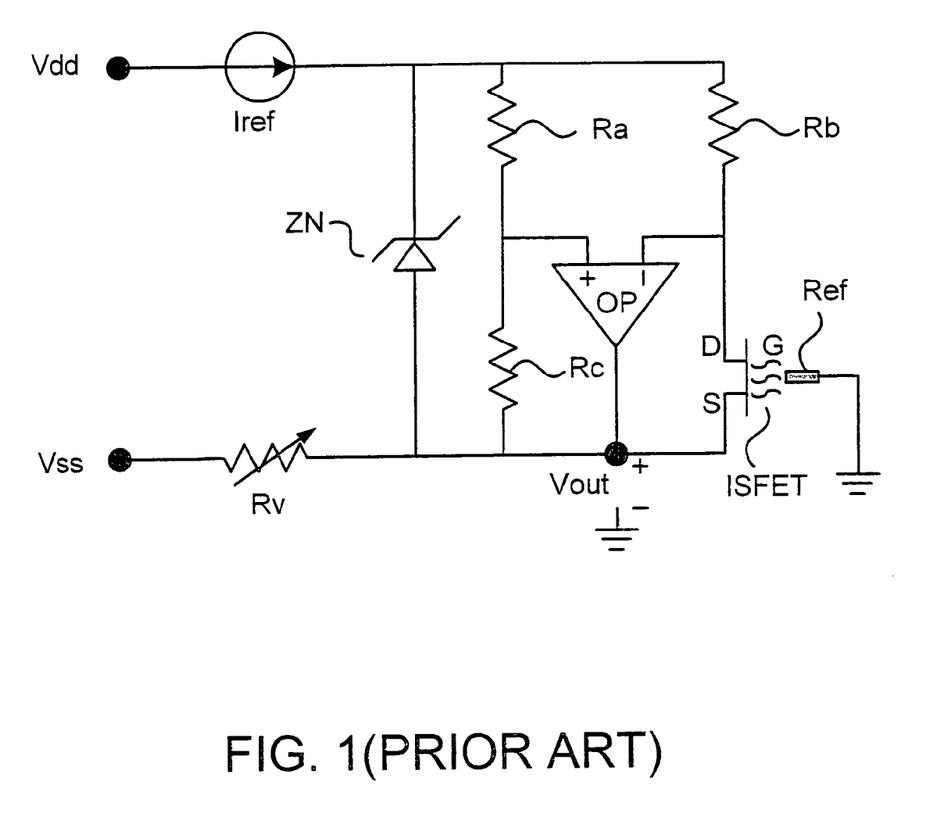
FIG. 1 shows a readout circuit disclosed in the prior art wherein the reference electrode is grounded and the bridge source is connected floatingly.

The issued methods use the constant voltage/constant current and the readout circuit configuration with floating reference electrodes to measure the ion concentration of a solution. As an example, let us consider the readout circuit configuration with grounded reference electrode and bridge-type floating source in FIG. 1. This circuit includes a bridge-type configuration consisting a current source Iref, a constant voltage source (where voltage is adjusted by a potentiometer Rv), and an operational amplifier OP, wherein the zener diode ZN provides a reference voltage of a specific voltage value, while the amplifier OP, resistors Ra, Rb, and Rc and the ISFET form a bridge network. Because of the balance of the bridge-type architecture and the virtual short circuit of the input terminals of the operational amplifier, the constant voltage VDS of the ISFET will be generated; then the constant current IDS passing through the ISFET will be determined by the resistor Rb. The advantage of this architecture is that the reference electrode is grounded so that only one common reference electrode is required to perform the multiple and simultaneous detection of ions by means of ISFETs. Since the Zener diode ZN with floating potentials at both terminals is fabricated in a special technological process, processing of this circuit is not compatible with a standard CMOS technology.

SUMMARY OF THE INVENTION

In view of the problems of the prior art, the present invention discloses an ion sensing circuit with body effect reduction. It is a read-out circuit for hydrogen ion sensitive ISFETs, designed as a bridge-type floating source configuration, which is used to solve the problem of integrating an ISFET and a readout circuit in a standard CMOS technology.

The following description of the content and embodiments of the invention is to demonstrate and explain the principle of the invention as well as to provide a further explanation of the claims of the invention.

According to the exemplary embodiments of invention, the bridge-type readout circuit with body effect reduction includes: a bridge-type floating source circuit that is provided with an input and output terminal, and an ISFET having a reference electrode coupled to the ground, wherein one terminal of the ISFET is coupled with the output terminal of the bridge-type circuit; a current mirror is coupled with the bridge-type floating source circuit and consists of a first transistor and a second transistor, for providing a current to the bridge-type circuit; a third transistor connected to the current mirror, for receiving the operating current provided by the current mirror equal to that provided to the ISFET; and a differential amplifying circuit, wherein one input terminal of the amplifying circuit is an input for a reference voltage, and the other input terminal is coupled with the output of the bridge-type circuit, to generate a differential voltage provided to the input of the bridge-type circuit, thereby enabling the ISFET to operate under constant current and constant voltage conditions.

According to the exemplary embodiments of the invention, the third transistor is an NMOS transistor with its gate controlled by a controllable external voltage VB.

According to the exemplary embodiments of the invention, the bodies of the ISFET and of the third transistor are both connected to the terminal of the most negative voltage.

According to the exemplary embodiments of the invention, the ISFET and the third transistor are matched with each other on the same p-type base.

According to the exemplary embodiments of the invention, an output signal of the bridge-type readout circuit with body effect reduction is constructed to solve the problem of integration of the ISFET and the readout circuit in a standard CMOS technology. Meanwhile, the exemplary embodiments of the invention adopting the differential output configuration can compensate for the undesired effect of the ISFET time and temperature drift at the same time. According to the exemplary embodiments of the invention, it does not require any complicated hardware and the corresponding calculations, and it is suitable for using in all ISFET-type sensors.

The specific characteristics and advantages of the invention will be discussed in detail in the embodiments herein, which is enough to make those skilled in the art to understand the content of the invention and implement it accordingly. Moreover, following the disclosure, the claims and the drawings of the invention, those skilled in the art can easily understand the relative objects and advantages of the invention.

Further scope of applicability of the present invention will become apparent from the detailed description given. However, it should be understood that the detailed description and specific examples, while indicating the preferred embodiments of invention, are given by way of illustration only, since various changes and modifications within the spirit and scope of the invention from this detailed description will become apparent to those skilled in the art.

BRIEF DESCRIPTION OF THE DRAWINGS

The present invention will become more fully understood from the detailed description given below for illustration only, and this is not limitative to the present invention, wherein.

DETAILED DESCRIPTION OF THE INVENTION

To facilitate further understanding of the object, construction, characteristics and functions of the invention, a detailed description with reference to the embodiments is given in the following.

Figure 2:
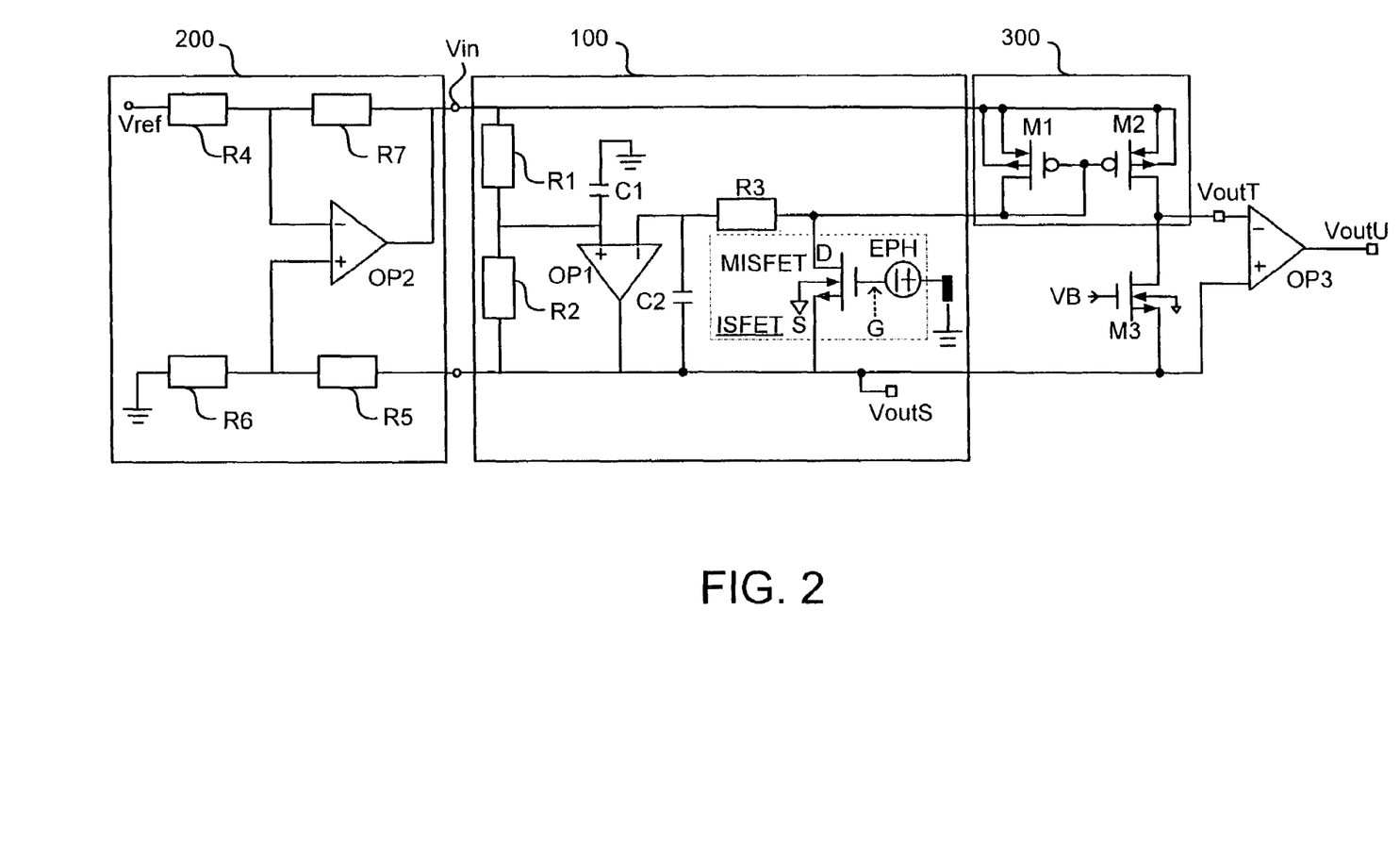
FIG. 2 is an embodiment of bridge-type readout circuit with body effect reduction configuration disclosed in the invention.

Referring to FIG. 2, the electronic circuit for ion sensors with the body effect reduction disclosed in the invention is a kind of readout circuit in a bridge-type configuration. The variation in the threshold voltage VTH can be recorded at the source terminal by using the bridge construction in a part of the bridge-type floating source circuit, grounding the reference electrode Ref, and connecting it to the source floatingly.

The sensor connected to the bridge-type floating source circuit can be directly exposed to the solution. As long as the species to be measured react with the acceptor on the ion sensing film, a change in the potential is observed at the ion sensing film/electrolyte interface recorded at the output terminal. An ISFET is a kind of ion sensing element, whose threshold voltage depends on the activity of the ions in the electrolyte.

As shown in FIG. 2, the bridge-type readout circuit with the body effect reduction disclosed in the invention includes a bridge sensing circuit 100, a differential amplifying circuit 200, a current mirror 300, and a third transistor M3. The bridge-type floating source circuit 100 is provided with an input terminal Vin and an output terminal VoutS. The circuit further includes an ISFET with a reference electrode Ref connected to the ground terminal, and one terminal of the ISFET is coupled to the output terminal VoutS for putting out the ion concentration. The differential amplifying circuit 200 has one input terminal with a reference voltage, and the other input terminal is coupled to the output terminal VoutS of the bridge-type floating source circuit 100 for generating a differential voltage to the input terminal Vin, thereby enabling the ISFET to be operated under constant current and voltage. The current mirror 300 coupled to the bridge-type floating source circuit 100 consists of a first transistor M1 and a second transistor M2, for providing a current to the bridge sensing circuit 100. In addition, M1 and M2 may be p-type metal oxide semiconductor (PMOS) transistors. A third transistor M3 connected to the current mirror 300 can be a gate voltage controlled N-type metal oxide semiconductor (NMOS) transistor, wherein its gate, controlled by an external applied controllable voltage VB, receives the operating current provided by the current mirror identical to the current provided for the ISFET.

The bodies of the ISFET and the third transistor M3 are connected to the terminal of the most negative voltage. The ISFET and the third transistor M3 are matched with each other on the same p-type base, to achieve an output signal free of the body effect.

As shown in FIG. 2, the bridge-type floating source circuit 100 consists of a first resistor R1, a second resistor R2, a third resistor R3, an ISFET, and a first amplifier OP1. The first amplifier OP1 is an operational amplifier. The first resistor R1 is connected to the second resistor R2 in series, and the third resistor R3 is coupled between the negative input terminal of the first amplifier and the drain of the ISFET. The positive input terminal of first amplifier OP1 is coupled between the first resistor R1 and the second resistor R2; its negative input terminal is coupled to the resistor R3 and the drain of the ISFET and its output terminal is coupled between the second resistor R2 and the source of the ISFET. The reference electrode Ref of the ISFET is grounded and its source is floatingly connected.

Because of the virtual short circuit characteristic of the operational amplifier, when the circuit is balanced, the drain-source voltage of the ISFET remains unchanged despite the variation of the ion concentration in the electrolyte. The operating voltage of the ISFET is determined by the voltage division of the first resistor R1 and the second resistor R2, and the operating current of the ISFET is provided by the first transistor M1. Therefore, the ISFET can work in the operating areas of constant current and constant voltage.

The constant voltage is input through the input terminal Vin, and the ion concentration is read out by the output terminal VoutS. The differential amplifying circuit 200 consists of a second amplifier OP2 and four resistors (R4, R5, R6 and R7), wherein the second amplifier OP2 is an operational amplifier.

A first capacitor C1 is coupled between the positive input terminal of the first amplifier OP1 and the ground terminal, and a second capacitor C2 is coupled between the negative input terminal and the output terminal of OP1. Both capacitors are used as bypass capacitors.

The differential amplifying circuit 200 has two input voltages: one is the reference voltage Vref, output to the negative input terminal of the second amplifier OP2 via the fourth resistor R4, and the other is the input voltage coming from the output terminal of the bridge sensing circuit 100, output to the positive input terminal of the second amplifier OP2 via the resistor R5. The sixth resistor R6 is coupled between the positive input terminal of the second amplifier OP2 and the ground terminal. The seventh resistor R7 is coupled between the negative input terminal and the output terminal of the second amplifier OP2.

In another embodiment, the aforementioned bridge-type readout circuit further includes a differential amplifying circuit constructed by a third amplifier OP3. The positive input terminal of the circuit is coupled to the output terminal VoutT, and its negative input terminal is coupled to the output terminal VoutS, wherein the output terminal VoutS is the output terminal for the source voltage and the output terminal VoutT is an output terminal for a signal used for the body effect reduction. The output terminal VoutU of the amplifier OP3 is an output for a signal used for the body effect reduction.

To detect the ion concentration in the solution, the sensor in the circuit as shown in FIG. 2 is operated in the constant voltage and constant current mode, wherein the input terminals Vin and S remain in a floating state:

$$Vin - V(S) = -Vref$$

Under such a condition, the constant voltage is given by $$V_{DS,MISFET} = \frac{R2}{R1+R2}|Vref|$$

Meanwhile, the current is fixed by keeping the VGS of the first transistor M1 constant: $I_{DS,MISFET} = I_{DS,M1}$ As the source voltage is influenced by different ion concentrations, the bridge-type readout circuit is easily influenced by the body effect of the single-chip ISFET control micro-system. Therefore, the ISFET and the third transistor M3 are operated in the same drain current by the current mirror 300 (consisting of the first transistor M1 and the second transistor M2), and the bodies of both ISFET and M3 are connected to the most negative power supply of the system. Thus, the drain currents of MISFET and the third transistor M3 are equal. To simplify the analysis, we employ MOSFETs in the saturation region. Hence, $$I_{DS,MISFET} = I_{DS,M3}$$

$$K_p(V_{GS,MISFET} - V_{TH,MISFET})^2 = K_p(V_{GS,M3} - V_{TH,M3})^2$$

Assuming that the ISFET and the third transistor M3 are matched with each other on the same p-type substrate, then:

$$V_{GS,MISFET} - V_{GS,M3} = V_{TH,MISFET} - V_{TH,M3} - EPH - VoutS - $$

$$(VoutT - VoutS)$$

$$= V_{TH0,MISFET} + \gamma\left(\sqrt{2\phi_f + V_{SB,MISFET}} - \sqrt{2\phi_f}\right) - \left[V_{TH0,M3} + \gamma\left(\sqrt{2\phi_f + V_{SB,M3}} - \sqrt{2\phi_f}\right)\right]$$

$$VoutT = -EPH$$

wherein, EPH represents the electric potential formed at the electrolyte/oxide interface. An output signal independent of the body effect can be obtained by VoutT=−EPH.

Meanwhile, an output signal for compensating the undesired effects of temperature and time drift can be obtained by the third amplifier OP3 VoutU=VoutT−VoutS.

Figure 3:
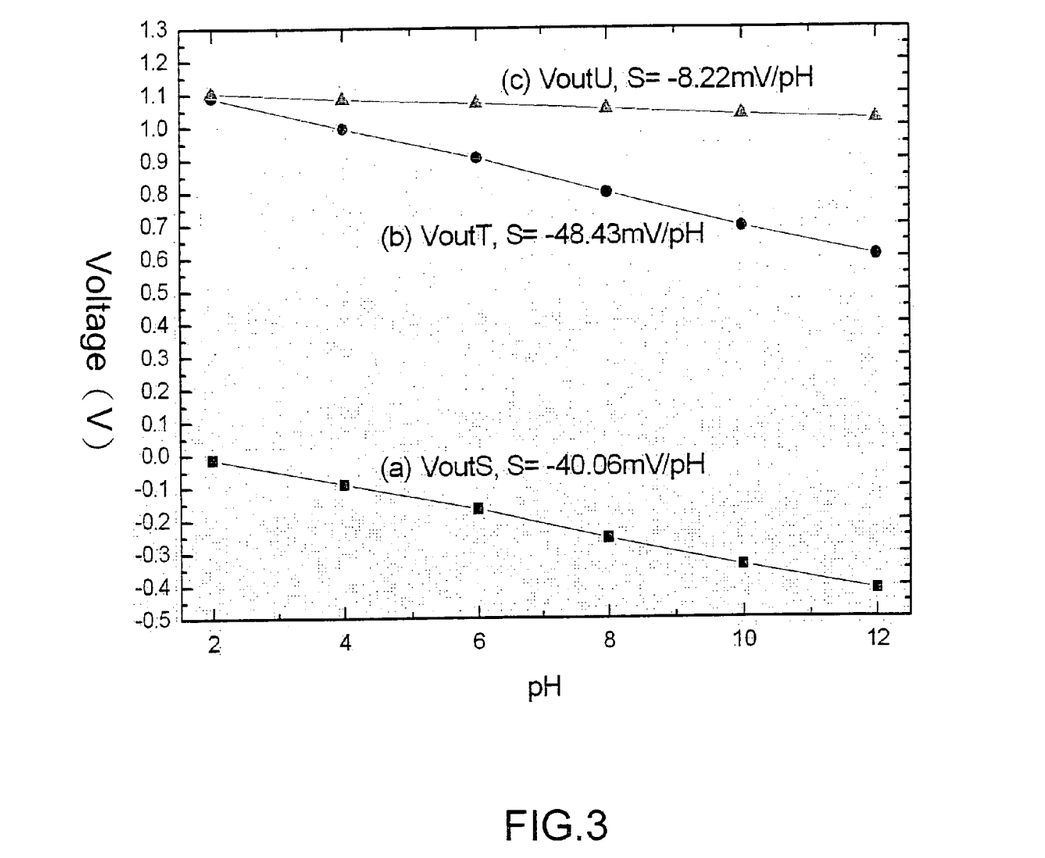
FIG. 3 is the measured output signal and calculated sensitivity for an ISFET type sensor exposed to electrolytes of pH ranging from 2 to 12 and operating in the bridge-type readout circuit with body effect reduction disclosed in the invention.

FIG. 3 shows the ISFET response and calculated sensitivity for the pH ranging from 2 to 12. The result shows that the slopes of characteristics (voltage-pH dependence) at VoutS, VoutT and VoutU are equal to −40.06 mV/pH, −48.43 mV/pH and −8.22 mV/pH, respectively. Then, the comparison of curve (a) and curve (b) demonstrates the improvement achieved by the reduction of the body effect.

Figure 4:
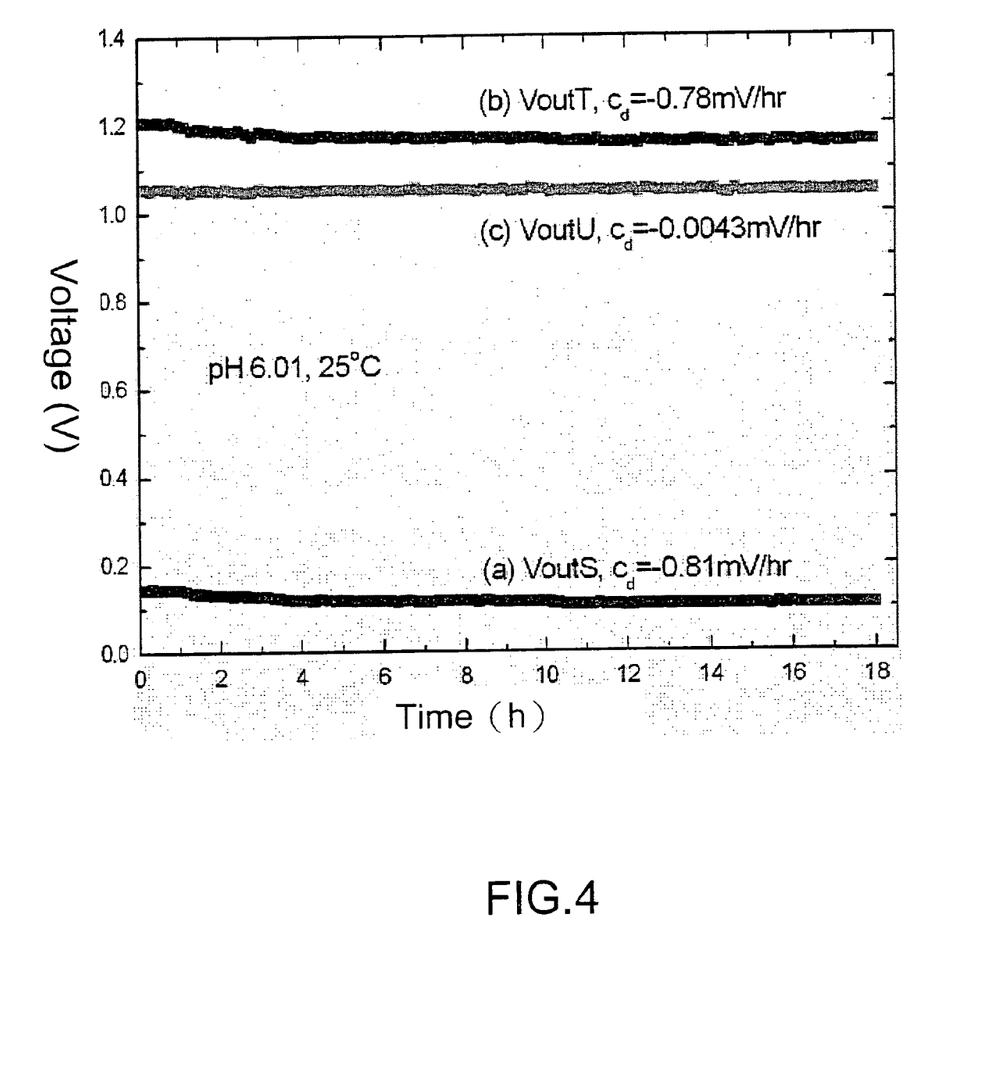
FIG. 4 is the characteristic measurement of the time drift before and after the compensation of the output signal of the bridge-type readout circuit disclosed in the invention; this measurement is carried out in a standard solution of pH=6 at 25±0.5° C. for 18 hours.

FIG. 4 is the characteristic measurement of the time drift before and after the compensation. This measurement is carried out in the standard solution of pH=6 at 25±0.5° C. for 18 hours. The time drift coefficient cd (mV/hr) is the variation of the VGS per unit time after the first 4 hours of stabilization. The result shows that the time drift coefficients of VoutS, VoutT, and VoutU are equal to −0.81, −0.78, and −0.0043 mV/hr, respectively. It can be seen that at the node VoutU, the time drift compensation performed by the circuit disclosed in the present invention largely reduces the time drift effect.

Figure 5:
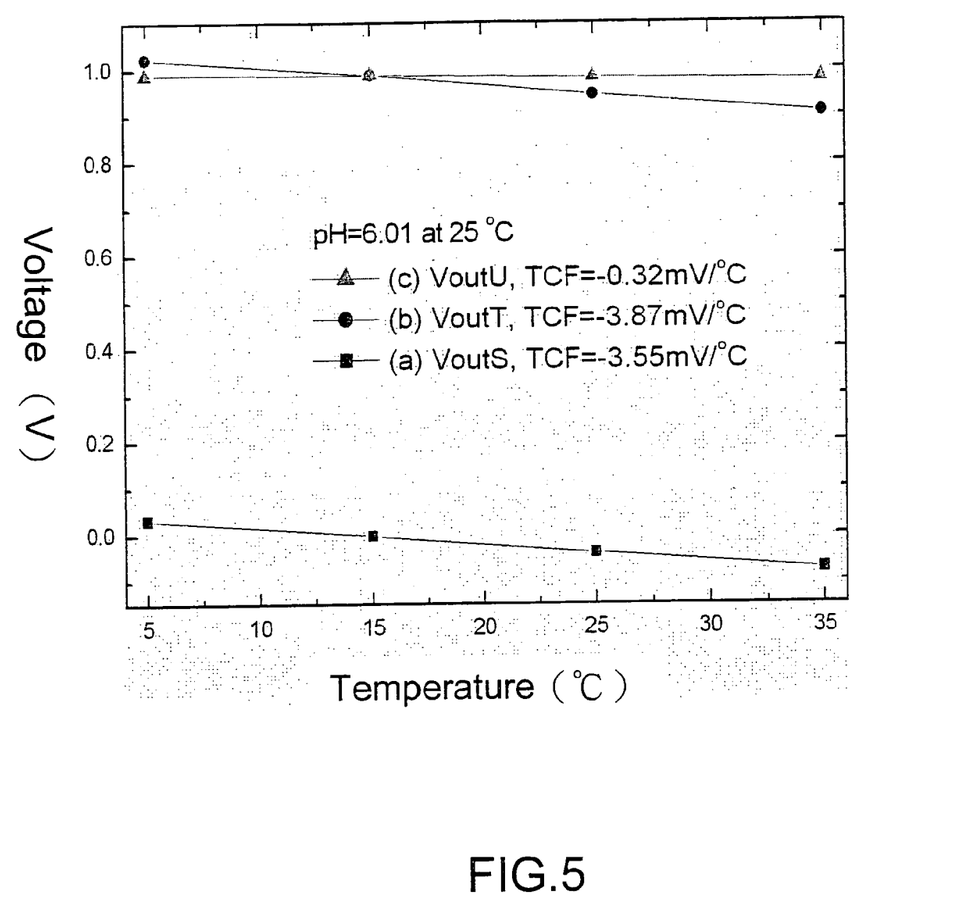
FIG. 5 compares the measured result of the temperature compensation. This measurement is carried out in the 5° C. to 35° C. temperature range (pH=6).

FIG. 5 compares the measured results of the temperature compensation. Under the condition of pH=6 and the temperature ranging from 5° C. to 35° C., the temperature coefficients obtained at VoutS, VoutT, and VoutU are −3.55 mV/° C., −3.87 mV/° C. and −0.32 mV/° C., respectively. Likewise, as in the case of time drift effect, the temperature drift can also be compensated. The results of compensation of temperature effect will be better if the ISFET and the third transistor M3 are matched with each other and manufactured on the same chip.

In general, in the case of a single ISFET type sensor, temperature and/or time drift compensation cannot be provided in any form. Therefore, in the aforementioned reference, to compensate for the temperature and time drift, a method based on a differential configuration with ISFETs of various sensitivities is proposed. As VoutS and VoutT reflect the same factors of temperature dependence, time drift and common mode noise, the invention only adopts one ISFET and one NMOS together with one differential configuration to achieve an output uninfluenced by temperature, time drift, or common mode noise, meanwhile diminishing the influence of body effect.

The invention discloses an electronic circuit for ion sensor with the body effect reduction, which uses only one ISFET and one differential output configuration, and can be applied to any kind of ISFET type sensor. It is not required to know any compensation parameter beforehand, its hardware is simple, and it is free of any redundant calculation programs. The measured data according to the embodiments of the invention show that good results are obtained regarding the compensation of temperature and time drift effects. Therefore, a significant improvement in the precision of measurement by means of ISFET type sensor is obtained.

It will be obvious that the same scheme may be varied in many ways. Such variations are not to be regarded as a departure from the spirit and scope of the invention, and all such modifications as would be obvious to one skilled in the art are intended to be included within the scope of the following claims.

What is claimed is:

1. An electronic circuit for ion sensors with the body effect reduction comprises:

a bridge-type readout circuit, provided with an input terminal and an output terminal, and with an Ion-sensitive field effect transistor (ISFET) having a reference electrode coupled to a ground terminal, wherein one terminal of the ISFET is coupled to the output terminal for outputting the voltage dependent on ion concentration, the bridge type readout circuit further comprises:

a first amplifier, wherein its negative input terminal is coupled to a drain of the ISFET and its output terminal is coupled to a source of the ISFET;

a first resistor coupled between the input terminal of the bridge sensing circuit and the positive input terminal of the first amplifier;

a second resistor coupled between the positive input terminal and the output terminal of the first amplifier, wherein the voltage division of the first and second resistors determines the operating voltage of the ISFET; and a third resistor coupled between the negative input terminal of the first amplifier and the drain of the ISFET;

wherein the first amplifier, the first resistor, the second resistor, the third resistor, and the ISFET construct a bridge network to make the ISFET operate under a condition of constant current and constant voltage;

a current mirror coupled to the bridge-type floating source circuit, which consists of a first transistor and a second transistor for providing a current to the bridge-type floating source circuit;

a third transistor connected to the current mirror, for receiving the operating current identical to the current provided for the ISFET; and a differential amplifying circuit, wherein one input terminal of the amplifying circuit is input with a reference voltage, and the other input terminal is coupled with the output of the bridge-type readout circuit, to generate a differential voltage to the input terminal of the bridge-type-readout circuit, thereby enabling the ISFET to operate under condition of constant current and constant voltage.

2. The bridge-type readout circuit according to claim 1, wherein the first and the second transistors are p-type metal oxide semiconductor (PMOS) transistors; their sources are connected to the bridge-type readout circuit; and the gates of the first transistor and the second transistor are connected with each other and then together connected to the drain of the first transistor.

3. The electronic circuit for ion sensor according to claim 1, wherein the third transistor is a gate voltage controllable n-type metal oxide semiconductor (NMOS) transistor.

4. The electronic circuit for ion sensor according to claim 1, wherein the bodies of the ISFET and the third transistor are both connected to the terminal of the most negative voltage.

5. The electronic circuit for ion sensor according to claim 1, wherein the ISFET and the third transistor are matched with each other on the same p-type base.

6. The electronic circuit for ion sensor according to claim 1, wherein a first capacitor is coupled between the positive input terminal of the first amplifier and the ground terminal.

7. The electronic circuit for ion sensor according to claim 1, wherein a second capacitor is coupled between the negative input terminal and the output terminal of the first amplifier.

8. The electronic circuit for ion sensor according to claim 1, wherein the differential amplifying circuit comprises:

a second amplifier having its output terminal coupled with the input terminal of the bridge sensing circuit;

a fourth resistor, coupled between the negative input terminal of the second amplifier and the reference voltage;

a fifth resistor, coupled between the output terminal of the bridge-type readout circuit and the positive input terminal of the second amplifier;

a sixth resistor, coupled between the positive input terminal of the second amplifier and the ground terminal; and a seventh resistor, coupled between the output terminal and the negative input of the second amplifier.

9. The electronic circuit for ion sensor according to claim 1, further comprises a third amplifier, wherein its positive input terminal is coupled to the current mirror, and its negative input terminal is coupled to the source of the third transistor.

* * * * *